(12) United States Patent
Milsom et al.

(10) Patent No.: US 8,430,890 B2
(45) Date of Patent: Apr. 30, 2013

(54) METHOD AND APPARATUS FOR ENDOSCOPICALLY TREATING RECTAL PROLAPSE

(76) Inventors: Jeffrey Milsom, New York, NY (US); Howard Riina, Scarsdale, NY (US); J. Fredrick Cornhill, New York, NY (US)

( * ) Notice: Subject to any disclaimer, the term of this patent is extended or adjusted under 35 U.S.C. 154(b) by 981 days.

(21) Appl. No.: 12/263,774

(22) Filed: Nov. 3, 2008

(65) Prior Publication Data

US 2009/0156996 A1   Jun. 18, 2009

Related U.S. Application Data

(60) Provisional application No. 60/985,009, filed on Nov. 2, 2007.

(51) Int. Cl.
*A61B 17/10* (2006.01)
(52) U.S. Cl.
USPC .......................................................... 606/139
(58) Field of Classification Search .................. 606/139, 606/144–147
See application file for complete search history.

(56) References Cited

U.S. PATENT DOCUMENTS

| | | | |
|---|---|---|---|
| 5,323,790 A | 6/1994 | Guhle et al. | |
| 5,458,608 A | 10/1995 | Wortrich | |
| 6,036,641 A | 3/2000 | Taylor et al. | |
| 6,626,916 B1* | 9/2003 | Yeung et al. | 606/139 |
| 2003/0208100 A1 | 11/2003 | Levy | |
| 2004/0106943 A1 | 6/2004 | Cappiello et al. | |
| 2005/0119524 A1 | 6/2005 | Sekine et al. | |
| 2006/0030884 A1 | 2/2006 | Yeung et al. | |
| 2007/0066869 A1 | 3/2007 | Hoffman | |
| 2008/0015614 A1* | 1/2008 | Kaleta et al. | 606/144 |
| 2008/0103361 A1 | 5/2008 | Makower et al. | |
| 2008/0228030 A1* | 9/2008 | Godin | 600/106 |

FOREIGN PATENT DOCUMENTS

WO    WO 2005/000111    1/2005

* cited by examiner

*Primary Examiner* — Gregory Anderson
(74) *Attorney, Agent, or Firm* — Pandiscio & Pandiscio

(57) ABSTRACT

In one form of the invention, there is provided a method for treating rectal prolapse, the method comprising: inserting an expandable element into a prolapsed rectum via the anus; expanding the expandable element so that the expandable element securely engages the rectum; advancing the expanded element distally so as to return the prolapsed rectum to its normal, non-prolapsed state; and securing the rectum to supporting tissue whereby to retain the rectum in its normal, non-prolapsed state. In another form of the invention, there is provided an endoscope assembly for treating rectal prolapse, the endoscope assembly comprising: an endoscope; a balloon catheter; and a tacker; wherein the endoscope, balloon catheter and tacker are mounted together for insertion as a unit.

20 Claims, 14 Drawing Sheets

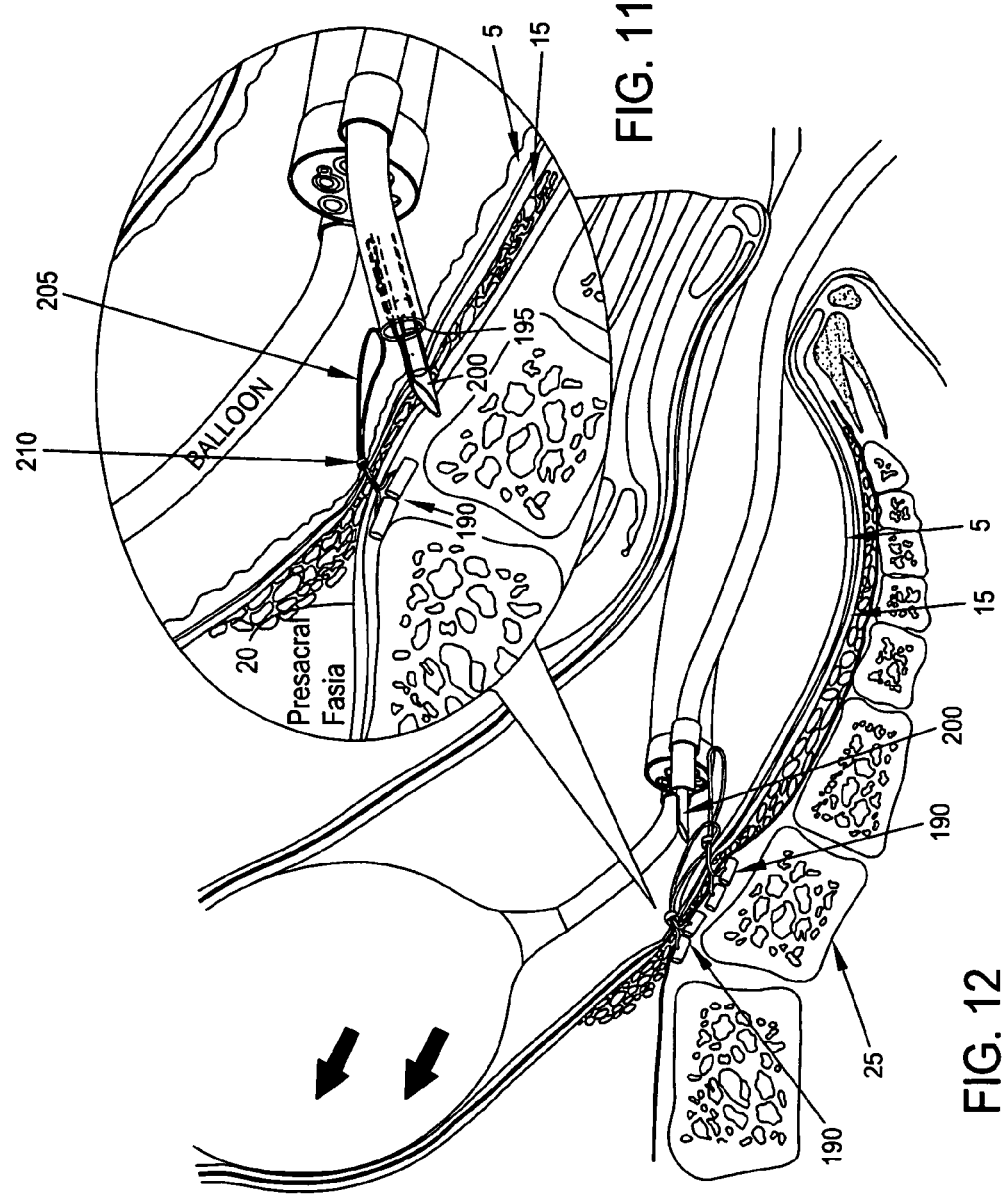

METHOD AND APPARATUS FOR ENDOSCOPICALLY TREATING RECTAL PROLAPSE

REFERENCE TO PENDING PRIOR PATENT APPLICATION

This patent application claims benefit of pending prior U.S. Provisional Patent Application Ser. No. 60/985,009, filed Nov. 02, 2007 by Jeffrey Milsom et al. for ENDOSCOPIC RECTOPEXY, which patent application is hereby incorporated herein by reference.

FIELD OF THE INVENTION

This invention relates to surgical methods and apparatus in general, and more particularly to surgical methods and apparatus for treating rectal prolapse.

BACKGROUND OF THE INVENTION

Rectal prolapse is a medical condition in which the walls of the rectum are not properly held in place, so that the rectum prolapses towards the anus and, in many cases, through the anal sphincter and outside the body.

There are three primary conditions which fall under the general category of rectal prolapse: (i) where the entire rectum protrudes through the anus (i.e., so-called "full thickness rectal prolapse"); (ii) where only the rectal mucosa prolapses (i.e., so-called "mucosal prolapse"); and (iii) where the rectum may collapse but not protrude through the anus (i.e., so-called "internal intussusception"). Rectal prolapse may be caused by a variety of conditions, e.g., advanced age, long term straining during defecation, pregnancy and childbirth, etc., and is typically characterized by a progression of symptoms, e.g., prolapse during bowel movements, prolapse during muscular stress (e.g., sneezing), prolapse during routine activities (e.g., walking) and, finally, chronic prolapse in which the rectum ceases to retract.

Mild cases of rectal prolapse can sometimes be treated secondarily, i.e., by reducing rectal straining through dietetic or pharmaceutical approaches. However, more severe cases of rectal prolapse must generally be treated surgically, either through abdominal surgery or perineal surgery. In any case, such surgery is substantial and traumatic in nature.

Thus there is a need for a new and improved approach for treating rectal prolapse, wherein the surgery is performed endoscopically so as to minimize trauma for the patient.

SUMMARY OF THE INVENTION

This and other objects of the present invention are addressed by the provision and use of a new and improved approach for treating rectal prolapse, wherein the surgery is performed endoscopically so as to minimize trauma for the patient.

In one form of the invention, there is provided a method for treating rectal prolapse, the method comprising:

inserting an expandable element into a prolapsed rectum via the anus;

expanding the expandable element so that the expandable element securely engages the rectum;

advancing the expanded element distally so as to return the prolapsed rectum to its normal, non-prolapsed state; and securing the rectum to supporting tissue whereby to retain the rectum in its normal, non-prolapsed state.

In another form of the invention, there is provided an endoscope assembly for treating rectal prolapse, the endoscope assembly comprising:

an endoscope;

a balloon catheter; and a tacker;

wherein the endoscope, balloon catheter and tacker are mounted together for insertion as a unit.

In another form of the invention, there is provided an endoscope assembly for treating rectal prolapse, the endoscope assembly comprising:

an endoscope;

a rectum-gripping and advancing mechanism; and a tacker;

wherein the endoscope, the rectum-gripping and advancing mechanism, and the tacker are mounted together for insertion as a unit;

and further wherein the rectum gripping and advancing mechanism is selected from the group consisting of a balloon catheter, expandable arms, and an expandable frame.

BRIEF DESCRIPTION OF THE DRAWINGS

These and other objects and features of the present invention will be more fully disclosed in, or rendered obvious by, the following detailed description of the preferred embodiments of the invention, which is to be considered together with the accompanying drawings wherein like numbers refer to like parts and further wherein:

FIGS. 10-12 are schematic views showing the tacker of the novel endoscope assembly securing the rectum to supporting tissue;

DETAILED DESCRIPTION OF THE OF THE PREFERRED EMBODIMENTS OF THE INVENTION

Figure 1:
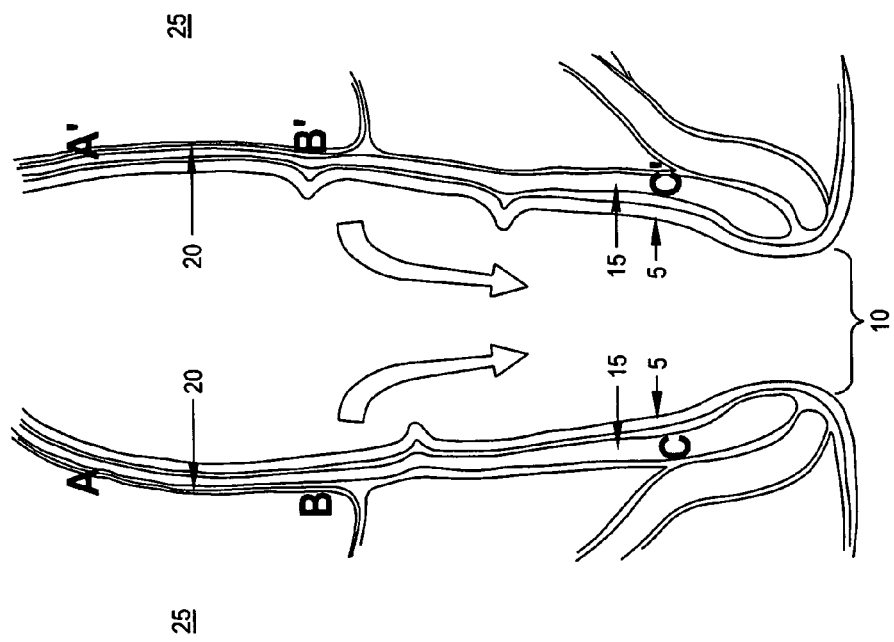
FIG. 1 is a schematic view of normal rectal anatomy, as seen in coronal view.
Figure 2:
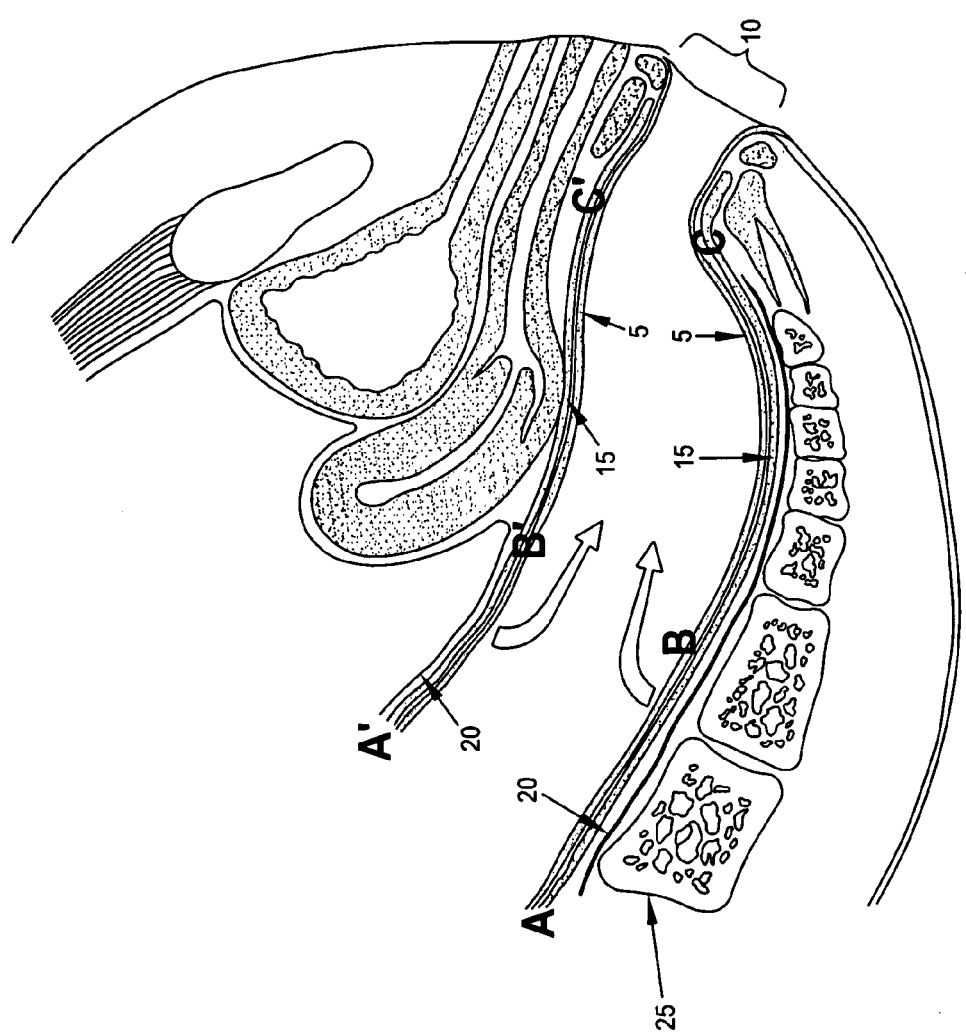
FIG. 2 is a schematic view of normal rectal anatomy, as seen in mid-sagittal view.

Looking first at FIGS. 1 and 2, there is shown a schematic view of normal rectal anatomy. More particularly, it will be seen that the rectum 5 generally comprises an elongated tubular structure terminating in the anus 10. Along its length, rectum 5 is lined by the mesorectum 15, i.e., the mesentery of the rectum. Along part of its length, mesorectum 15 lies adjacent to the presacral fascia 20 which lines the sacrum 25.

Figure 3:
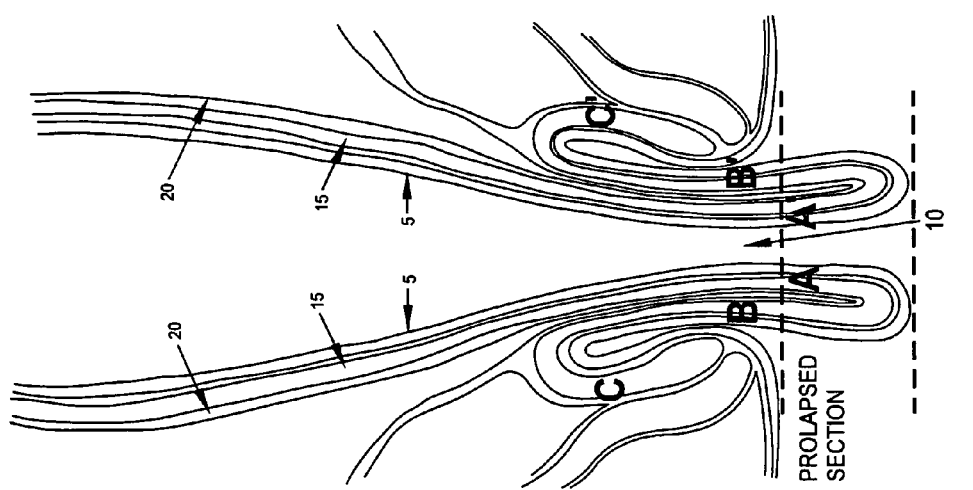
FIG. 3 is a schematic view of prolapsed rectal anatomy, as seen in coronal view.
Figure 4:
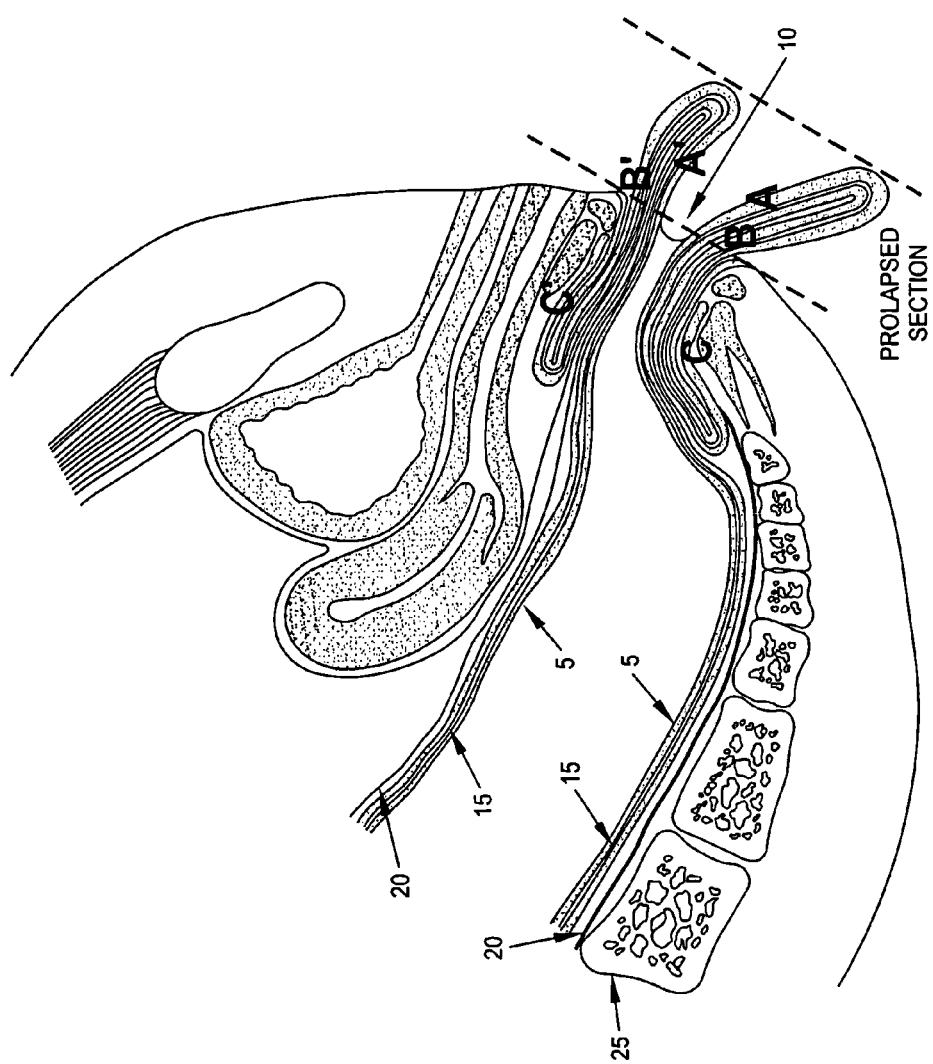
FIG. 4 is a schematic view of prolapsed rectal anatomy, as seen in mid-sagittal view.

In the case of a prolapsed rectum, and looking now at FIGS. 3 and 4, the walls of rectum 5 are not properly held in place, so that the rectum prolapses towards anus 10. In this respect it should be appreciated that FIGS. 3 and 4 show a so-called "full thickness rectal prolapse" (i.e., where the entire rectum protrudes through the anus), however, these views are intended to be merely exemplary and it should be appreciated that the present invention is applicable to other forms of rectal prolapse as well, i.e., "mucosal prolapse" where only the rectal mucosa prolapses and/or "internal intussusception" where the rectum may collapse but not protrude through the anus.

The present invention provides a new and improved approach for treating rectal prolapse, wherein the surgery is performed endoscopically so as to minimize trauma for the patient.

Figure 5:
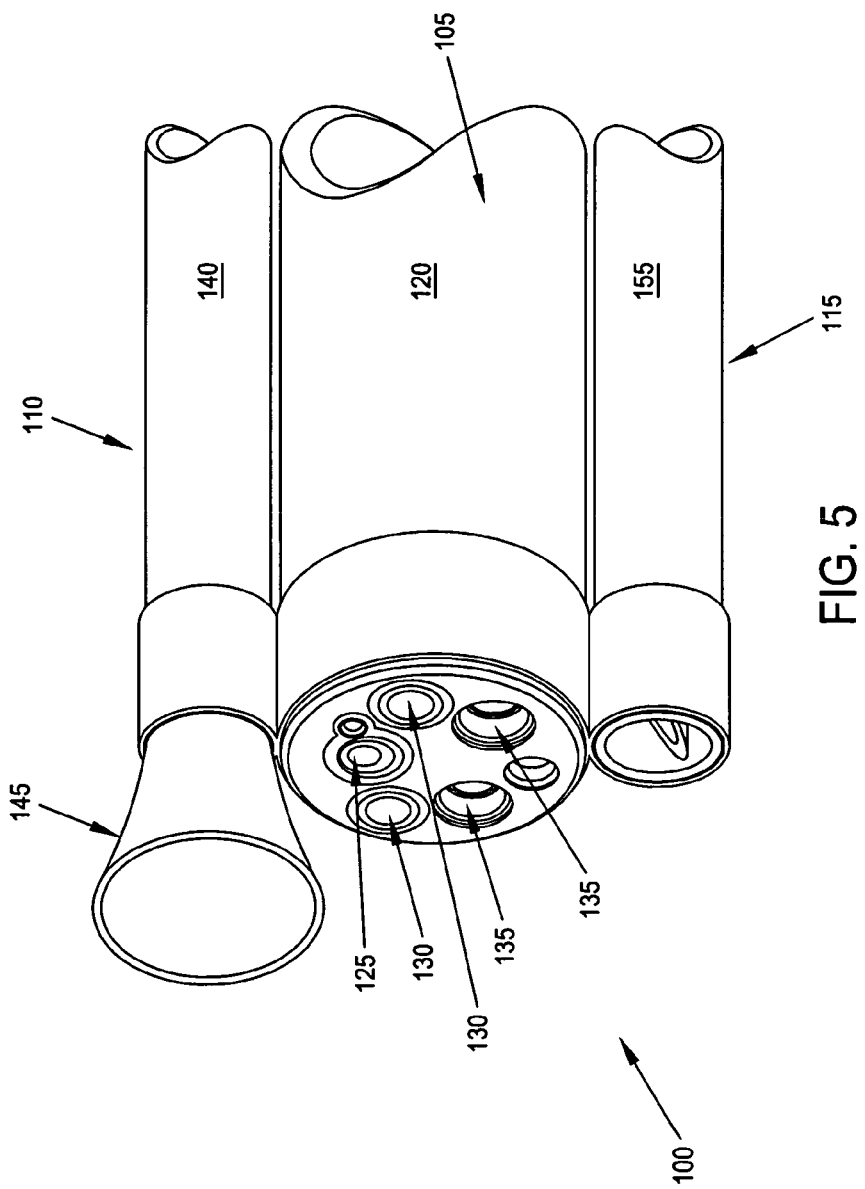
FIG. 5 is a schematic view of a novel endoscope assembly, wherein the novel endoscope assembly comprises an endoscope, a balloon catheter and a tacker.

More particularly, and looking now at FIG. 5, there is shown a novel endoscope assembly 100 formed in accordance with the present invention. Endoscope assembly 100 generally comprises an endoscope 105 for visualizing the interior of the rectum, a balloon catheter 110 for selectively deploying a balloon within the interior of the rectum, and a tacker 115 for selectively tacking the rectum to supporting structure, all as will hereinafter be discussed in further detail. Endoscope assembly 100 is preferably constructed so that endoscope 105, balloon catheter 110 and tacker 115 are mounted together for insertion into the rectum as a unit.

Endoscope 105 may comprise a conventional endoscope. By way of example but not limitation, endoscope 105 may comprise a shaft 120 comprising a viewing element 125, lighting elements 130, working lumens 135, etc.

Balloon catheter 110 may comprise a conventional balloon catheter. By way of example but not limitation, balloon catheter 110 may comprise a shaft 140 terminating in a distal end 145 from which a balloon (not shown in FIG. 5) may be selectively deployed, as will hereinafter be discussed in further detail.

Tacker 115 may comprise a conventional tacker for tacking tissue. By way of example but not limitation, tacker 115 may comprise a shaft 155 containing a tacking mechanism (not shown in detail in FIG. 5) for tacking tissue, as will hereinafter be discussed in further detail.

Figure 6:
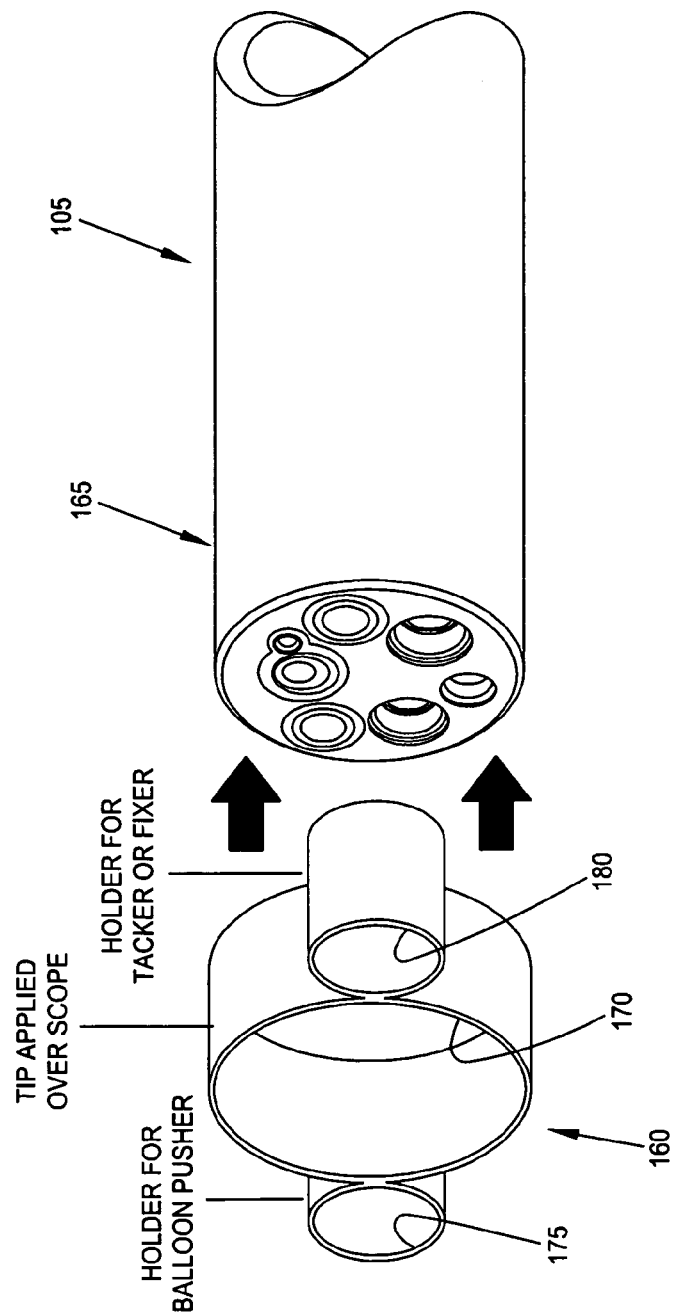
FIG. 6 is a schematic view showing how a distal mount may be secured to the distal end of a conventional endoscope in order to permit the balloon catheter and tacker to be mounted to the endoscope.

In one preferred form of the invention, and looking now at FIGS. 5 and 6, endoscope assembly 100 may be formed by securing a distal mount 160 to the distal end 165 of endoscope 105. To this end, distal mount 160 may comprise a central opening 170 sized to fit over distal end 165 of endoscope 105. Distal mount 160 preferably also comprises a first lateral opening 175 for slidably receiving shaft 140 of balloon catheter 110 therein, and a second lateral opening 180 for slidably receiving shaft 155 of tacker 115 therein.

Endoscope assembly 100 is preferably used in the following manner to endoscopically treat rectal prolapse.

Figure 7:
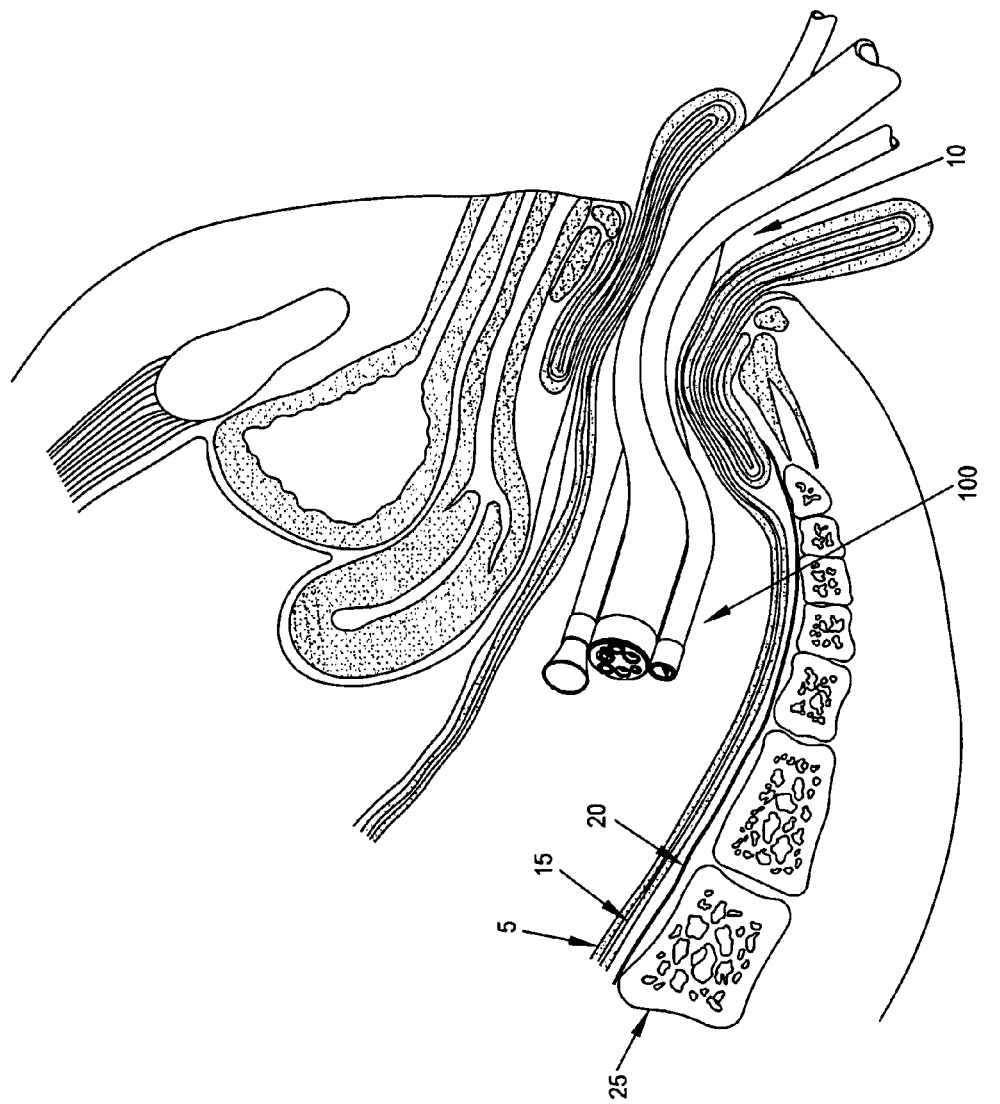
FIG. 7 is a schematic view showing the novel endoscope assembly of FIG. 5 deployed in the rectum.

First, and looking now at FIG. 7, endoscope assembly 100 is advanced into rectum 5 via anus 10.

Figure 8:
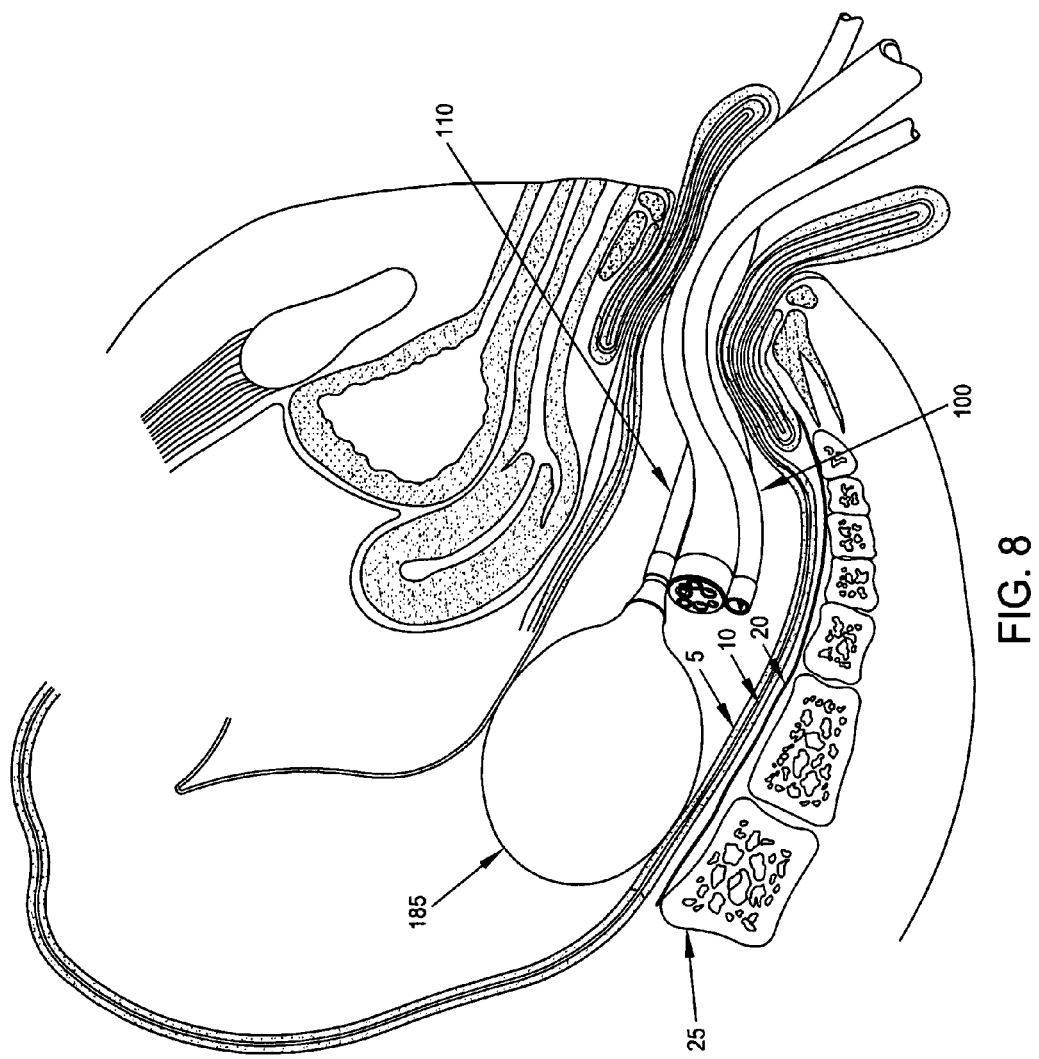
FIG. 8 is a schematic view like that of FIG. 7, except showing the balloon of the balloon catheter having been inflated.

Next, and looking now at FIG. 8, balloon 185 of balloon catheter 110 is inflated so as to securely engage, and thereby "grip", rectum 5.

Figure 9:
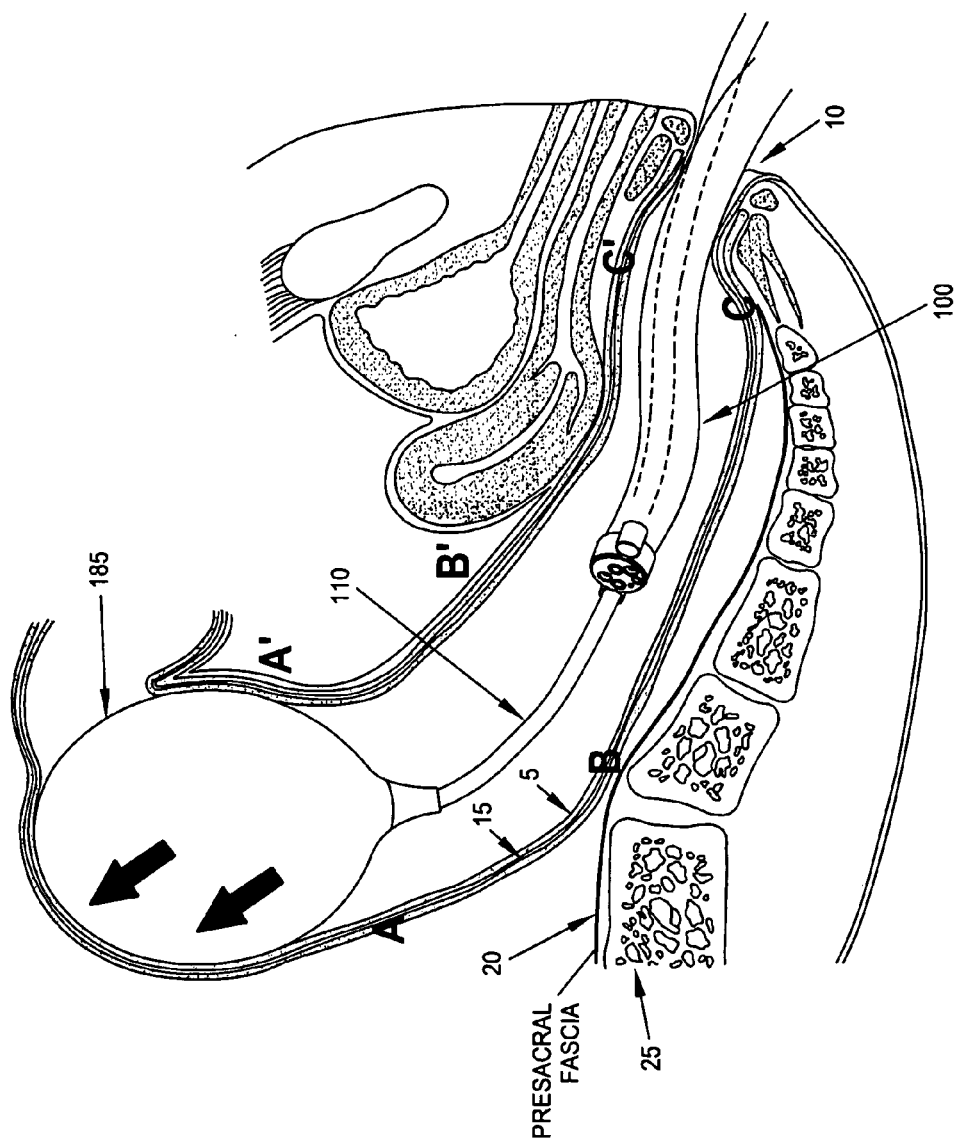
FIG. 9 is a schematic view like that of FIG. 8, except showing the balloon of the balloon catheter having been extended distally from the endoscope so as to reduce rectal prolapse.

Then, and looking now at FIG. 9, balloon catheter 110 is advanced distally relative to the remainder of endoscope assembly 100, e.g., by pushing on the proximal end of shaft 140 of balloon catheter 110, whereby to cause shaft 140 of balloon catheter 110 to slide distally within first lateral opening 175 of distal mount 160 and to cause balloon 185 to move distally within the body. As this occurs, the advancing balloon 185 of balloon catheter 110 carries with it rectum 5, since balloon 185 securely engages and grips rectum 5, thereby reducing the prolapse. Preferably, balloon catheter 110 is moved distally by a sufficient distance so as to return the prolapsed rectum to its normal, non-prolapsed state.

Figure 10:
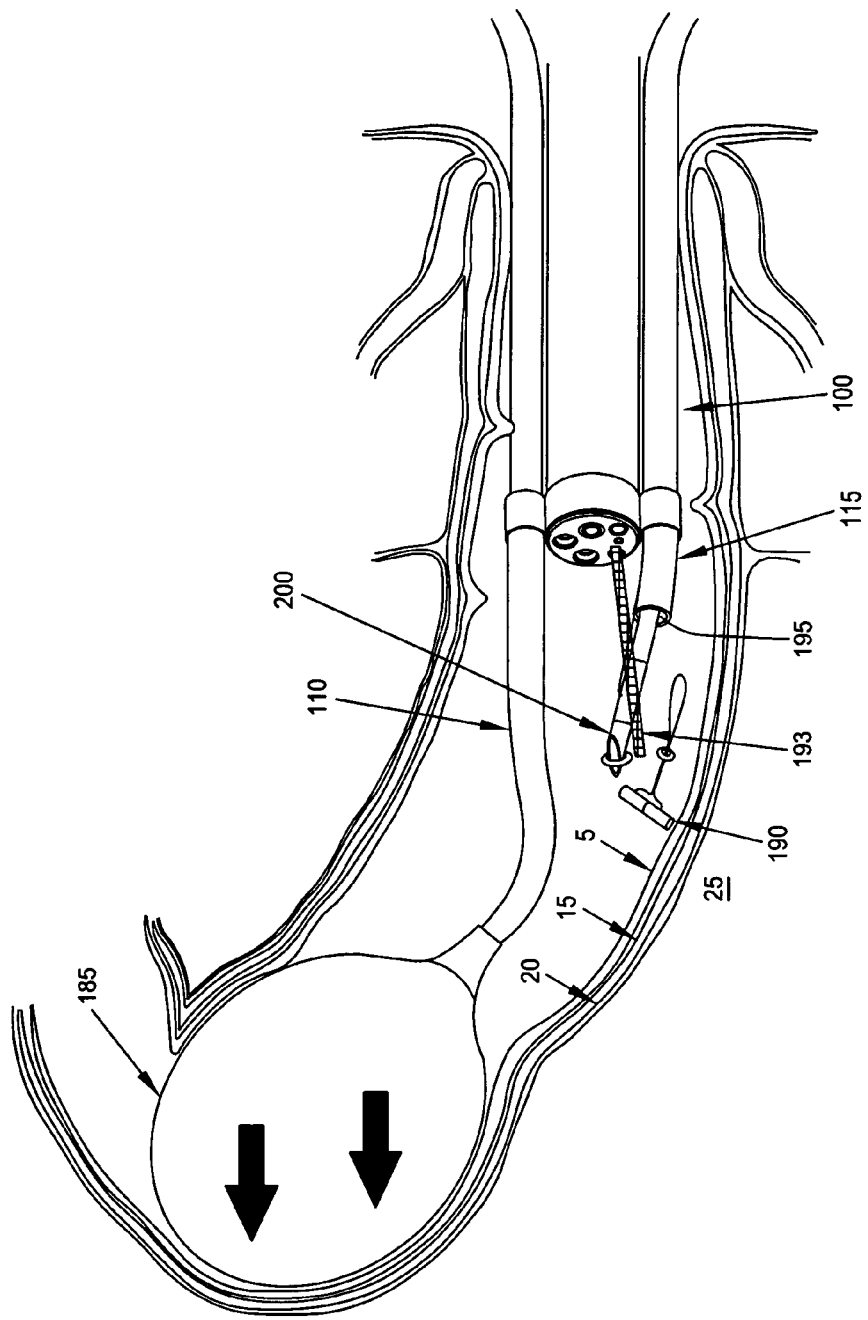

Then, and looking now at FIG. 10, tacker 115 is used to secure rectum 5 to supporting tissue, whereby to retain rectum 5 in its normal, non-prolapsed state.

In one preferred form of the invention, and looking now at FIGS. 10-12, tacker 115 is used to tack rectum 5 and mesorectum 15 to presacral fascia 20 using one or more tacks 190. In this respect it will be appreciated that it is generally desirable to secure rectum 5 and mesorectum 15 to presacral fascia 20, since the presacral fascia generally constitutes excellent supporting tissue. Of course, if desired, rectum 5 and mesorectum 15 may also be secured to other supporting tissue as well. To this end, an ultrasound probe 193 (shown in FIG. 10, but omitted from FIGS. 11 and 12 for viewing clarity) may be advanced through a working lumen 135 of endoscope 105 so as to locate the sacral promontory (or other satisfactory anatomical landmark), and then shaft 155 of tacker 115 may be advanced relative to the remainder of endoscope assembly 100 (e.g., by sliding shaft 155 of tacker 115 within second lateral opening 180 of distal mount 160) until the distal end 195 of tacker shaft 155 is proximate the tacking site. Then, a tacker needle 200 is advanced out of tacker shaft 155 and passed through rectum 5, mesorectum 15 and presacral fascia 20. Next, a tack 190 is ejected out of tacker needle 200, and then tacker needle 200 withdrawn back through presacral fascia 20, mesorectum 15 and rectum 5, leaving a length of filament 205 extending from tack 190 through the intervening tissue (i.e., through presacral fascia 20, mesorectum 15 and rectum 5) and into the interior of rectum 5. Filament 205 can then be tied off, or otherwise secured with a securement band 210, so as to secure rectum 5 and mesorectum 15 to presacral fascia 20. This process can then be repeated as necessary so as to set additional tacks into the tissue, whereby to secure the prolapsed rectum in its normal, non-prolapsed state.

Figure 13:
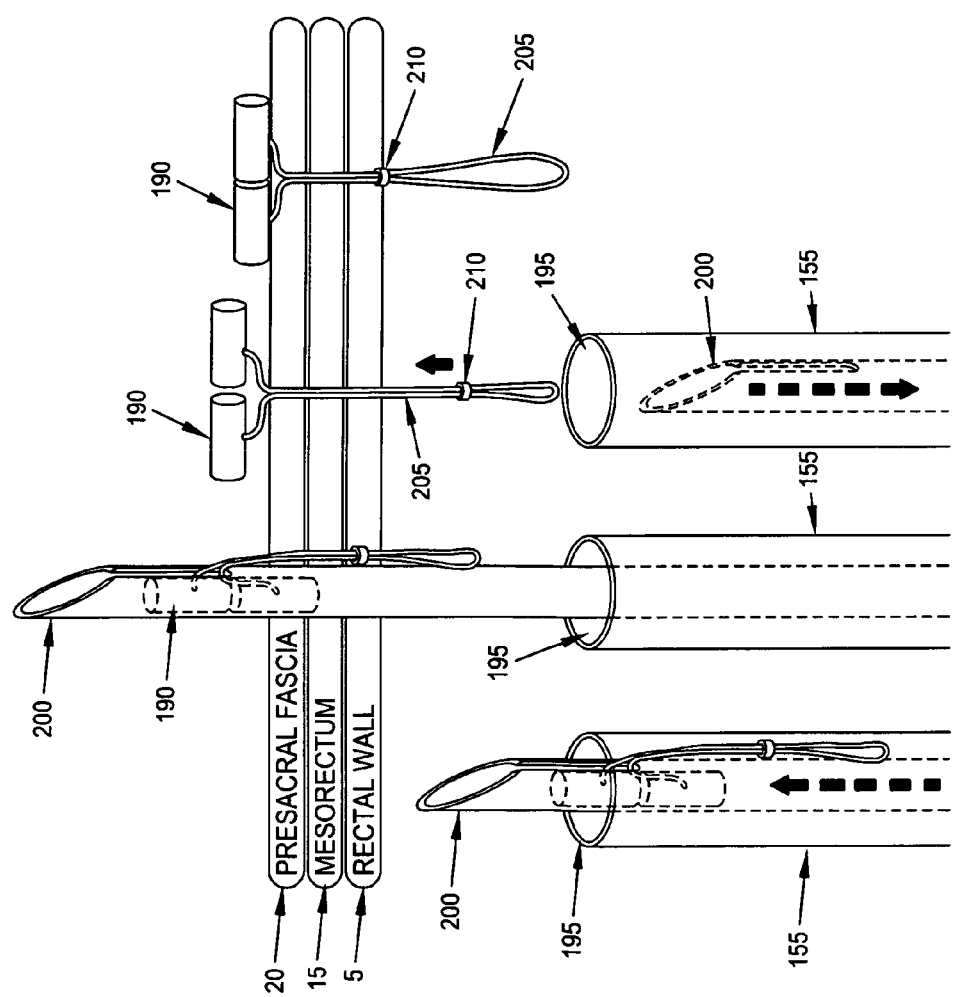
FIG. 13 is a schematic view showing operation of the tacker shown in FIGS. 10-12.

Further details of the operation of tacker 115 are shown in FIG. 13.

Thereafter, tacker 115 is retracted so that its needle 200 sits within tacker shaft 155, and then tacker shaft 155 is retracted so that its distal end 195 once again sits substantially adjacent to the distal end of endoscope 105. Then balloon 185 is deflated, and then balloon catheter 110 is retracted so that its distal end once again sits substantially adjacent to the distal end of endoscope 105. Then endoscope assembly 100 is withdrawn from the rectum via anus 10.

Figure 14:
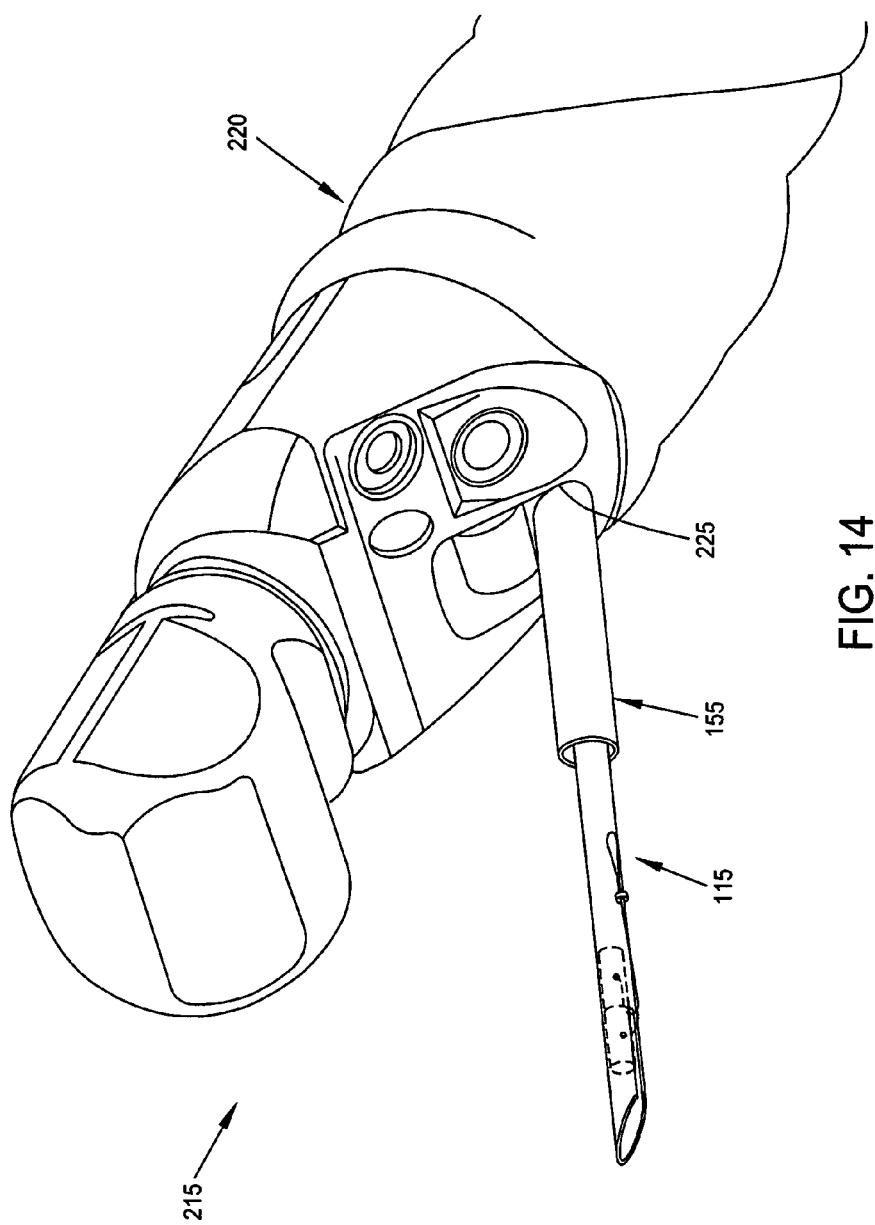
FIG. 14 is a schematic view showing a combined ultrasound probe/tacker unit.

Looking next at FIG. 14, there is shown a combined ultrasound probe/tacker unit 215. More particularly, combined ultrasound probe/tacker unit 215 generally comprises an ultrasound probe 220 having a working lumen 225 formed therein. Tacker 115 has its shaft 155 slidably disposed within working lumen 225 so that the tacker can be selectively advanced out of ultrasound probe 220. In this form of the invention, combined ultrasound probe/tacker unit 215 can be movably mounted to endoscope assembly 100 (e.g., by an appropriately configured distal mount 160), or combined ultrasound probe/tacker unit 215 can be advanced through a working lumen 135 of endoscope 105, or combined ultrasound probe/tacker unit 215 can be advanced into rectum 5 independently of endoscope 105.

It should also be appreciated that, if desired, balloon catheter 110 can be advanced through a working lumen 135 of endoscope 105, or balloon catheter 110 can be advanced into rectum 5 independently of endoscope 105.

Furthermore, it should also be appreciated that, if desired, tacker 115 can be advanced through a working lumen 135 of endoscope 105, or tacker 115 can be advanced into rectum 5 independently of endoscope 105.

Figure 15:
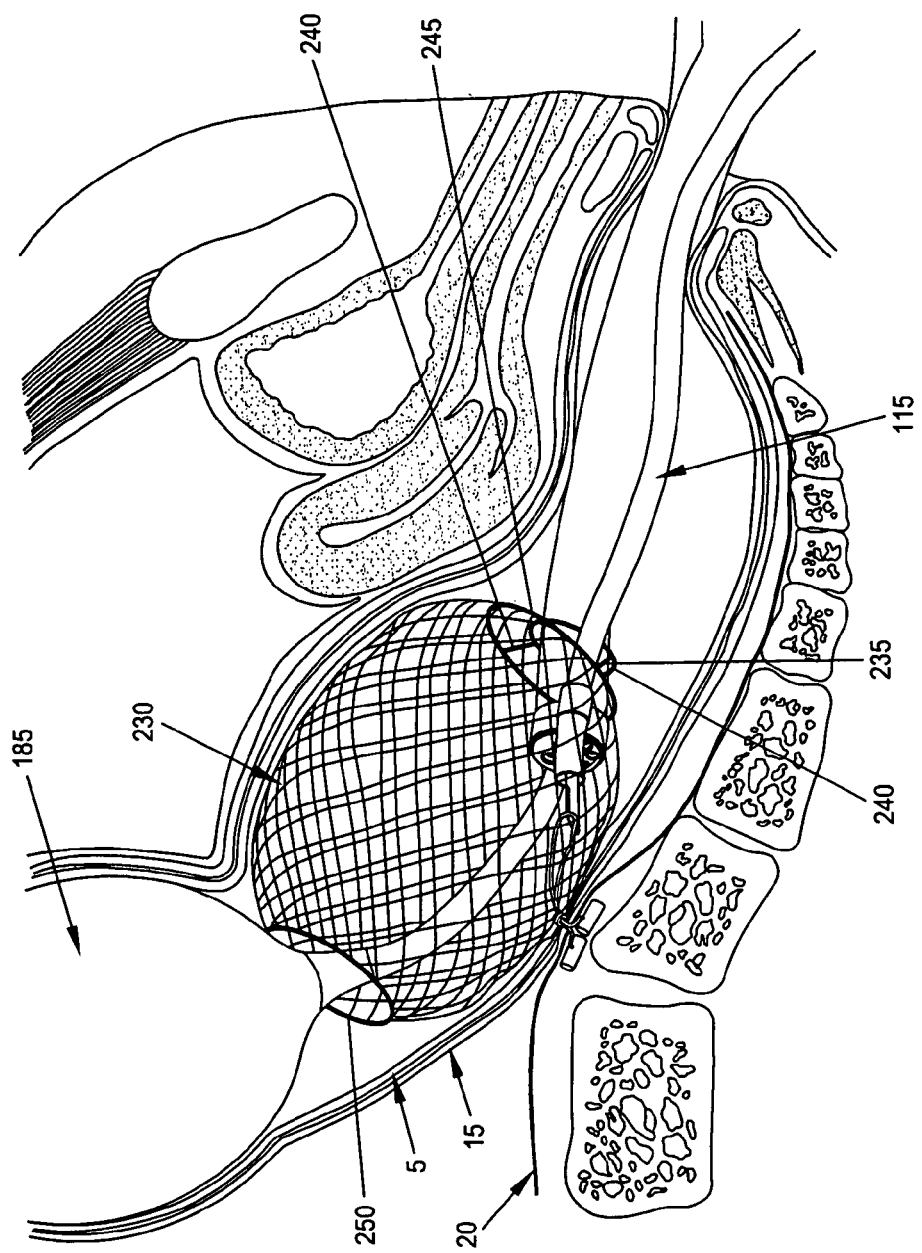
FIG. 15 is a schematic view showing an alternative approach for treating a prolapsed rectum.

Looking next at FIG. 15, in an alternative form of the invention, an expandable net 230 may be deployed within rectum 5 (e.g., after balloon 185 has been used to return the prolapsed rectum to its normal, non-prolapsed state but before tacker 115 has been used to secure rectum 5 to supporting tissue) in order to better hold rectum 5 in position while tacking occurs. In this respect it should also be appreciated that expandable net 230 can also serve to help anchor the endoscope and hold it in place while tacking is effected, thereby facilitating the tacking process. In one preferred form of the invention, expandable net 230 may comprise a collar 235 configured to ride over shaft 120 of endoscope 105, with struts 240 connecting collar 235 to a proximal support ring 245. Preferably, a distal support ring 250 is formed on the distal end of expandable net 230. It should be appreciated that various approaches can be used to hold expandable net 230 in a contracted position prior to expansion. By way of example but not limitation, expandable net 230 may be formed out of Nitinol, and a temperature transition used to transform expandable net 230 from its contracted position to its expanded position.

If desired, balloon catheter 110 can be replaced by an alternative rectum-gripping mechanism, e.g., wherein expandable arms, an expandable frame, etc. are erected within the rectum so as to grip the rectum prior to the distal movement necessary to return the prolapsed rectum to its normal, non-prolapsed state. In this respect it will be appreciated that while it is generally preferred to use a balloon for engaging and pushing the rectum, such alternative rectum-gripping mechanisms (e.g., expandable arms, an expandable frame, etc.) may offer the advantage of better engaging the tissue of the rectum and may provide mechanical advantage for pushing the rectum distally. In this respect it should also be appreciated that while it is generally preferred that the balloon and/or alternative rectum-gripping mechanisms be relatively atraumatic, it may also be desirable to provide tissue-gripping means to facilitate pushing the prolapsed rectum distally. To this end, where a balloon is used, it may be desirable to provide the balloon with a high-friction outer surface; and where expandable arms are used, it may be desirable to provide the arms with tissue-gripping elements (e.g., mechanical jaws, suction mechanisms, etc.); and where an expandable frame is used, it may be desirable to provide openings in the frame to facilitate tissue engagement, etc.

Furthermore, if desired, tacker 115 can be replaced by other tackers. In this respect it should be appreciated that the terms "tack" and "tacker" are intended to encompass substantially any mechanical structure which is capable of securing the rectum to supporting tissue. By way of example but not limitation, the terms "tack" and "tacker" are intended to encompass shaft-type tacks, legged staples, multi-part fasteners, tacks comprising a body having suture extending therefrom, etc.

Furthermore, if desired, tacker 115 can be replaced by appropriate endoscopic suturing apparatus, with the rectum being secured to supporting tissue using conventional suture.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for treating rectal prolapse, the method comprising:
   inserting an expandable element into a prolapsed rectum via the anus;
   expanding the expandable element so that the expandable element securely engages and thereby grips the rectum;
   advancing the expanded element distally so as to move the prolapsed rectum distally, thereby returning the prolapsed rectum to its normal, non-prolapsed position; and
   securing the rectum to supporting tissue whereby to retain the rectum in its normal, non-prolapsed position.

2. A method according to claim 1 wherein the method comprises the additional steps of;
   returning the expanded element to its contracted state; and
   withdrawing the expandable element from the rectum via the anus.

3. A method according to claim 1 wherein the expandable element comprises a balloon.

4. A method according to claim 3 wherein the balloon is part of a balloon catheter.

5. A method according to claim 4 wherein the balloon catheter is slidably mounted to an endoscope.

6. A method according to claim 5 wherein the rectum is secured to supporting tissue with a tacker, and further wherein the tacker is slidably mounted to the endoscope.

7. A method according to claim 1 wherein the expandable element comprises at least one selected from the group consisting of a balloon, expandable arms and an expandable frame.

8. A method according to claim 1 wherein the expandable element is expanded with a fluid.

9. A method according to claim 1 wherein the rectum is secured to supporting tissue with a tacker.

10. A method according to claim 1 wherein the rectum is secured to supporting tissue with at least one selected from the group consisting of a tack and suture.

11. A method according to claim 10 wherein the tack is selected from the group consisting of shaft-type tacks, legged staples, multi-part fasteners, and tacks comprising a body having suture extending therefrom.

12. A method according to claim 1 wherein the tack consists of at least one substantially rigid element having a suture attached thereto.

13. A method according to claim 1 wherein the tack further comprises a securement band for securing the suture.

14. A method according to claim 1 wherein the rectum is secured to supporting tissue by suturing.

15. A method according to claim 1 wherein the rectum is secured to the presacral fascia.

16. A method according to claim 1 wherein the securement location is determined by identifying an anatomical landmark.

17. A method according to claim 16 wherein the anatomical landmark is determined from a location within the rectum.

18. A method according to claim 16 wherein the anatomical landmark is identified by an ultrasound probe disposed within the rectum.

19. A method according to claim 16 wherein the anatomical landmark is identified by an endoscope disposed within the rectum.

20. A method according to claim 16 wherein the anatomical landmark is the sacral promontory.

\* \* \* \* \*